(12) United States Patent
Betts et al.

(10) Patent No.: US 12,161,069 B2
(45) Date of Patent: Dec. 10, 2024

(54) HIGH DENSITY RIGID MOLDED BODY OF COMPOSITE MYCOLOGICAL MATERIAL

(71) Applicant: Ecovative LLC, Green Island, NY (US)

(72) Inventors: Jeffrey Daniel Betts, Newtown, PA (US); Gregory John Tudryn, Hadley, MA (US); Courtney Elizabeth Hart, Adams, MA (US)

(73) Assignee: Ecovative LLC, Green Island, NY (US)

( * ) Notice: Subject to any disclaimer, the term of this patent is extended or adjusted under 35 U.S.C. 154(b) by 750 days.

(21) Appl. No.: 16/116,545

(22) Filed: Aug. 29, 2018

(65) Prior Publication Data

US 2019/0090436 A1 Mar. 28, 2019

Related U.S. Application Data

(62) Division of application No. 15/099,790, filed on Apr. 15, 2016, now Pat. No. 10,537,070.

(60) Provisional application No. 62/147,813, filed on Apr. 15, 2015.

(51) Int. Cl.
*C12N 1/14* (2006.01)
*A01G 18/00* (2018.01)

(52) U.S. Cl.
CPC .............. *A01G 18/00* (2018.02); *C12N 1/14* (2013.01)

(58) Field of Classification Search
CPC ............. C12N 1/00; C12N 1/14; A01G 18/00
USPC ........................ 47/1.1; 435/254.1, 171, 256.8
See application file for complete search history.

(56) References Cited

U.S. PATENT DOCUMENTS

| | | | |
|---|---|---|---|
| 1,979,176 | A | 10/1934 | Schicht |
| 2,509,984 | A | 5/1950 | Morrow |
| 2,657,647 | A | 11/1953 | Rapisarda |
| 2,723,493 | A | 11/1955 | Stoller |
| 2,815,621 | A | 12/1957 | Carter |
| 2,964,070 | A | 12/1960 | Linhardt |
| 3,268,606 | A | 8/1966 | Jaeger |
| 3,316,592 | A | 5/1967 | Forrest |
| 3,317,375 | A | 5/1967 | Molinet et al. |

(Continued)

FOREIGN PATENT DOCUMENTS

| | | |
|---|---|---|
| CN | 1059662 A | 3/1992 |
| CN | 1273249 A | 11/2000 |

(Continued)

OTHER PUBLICATIONS

Bartnicki-Garcia, "Cell wall chemistry, morphogenesis, and taxonomy of fungi", Annual Review Microbiol. (1968) 22(1): 87-108.

(Continued)

*Primary Examiner* — Peter M Poon
*Assistant Examiner* — Danielle A Clerkley
(74) *Attorney, Agent, or Firm* — Dority & Manning, P.A.

(57) ABSTRACT

A mycological composite material is made by inoculating a substrate of fibrous material with an inoculum of mycelial tissue; rolling the inoculated substrate into a roll; and thereafter incubating the rolled inoculated substrate for a time sufficient for the mycelial tissue to grow hyphae that enmesh with the substrate to form a cohesive unified filamentous network with the rolled inoculated substrate being characterized in being flexible. The rolled inoculated substrate is subsequently processed by subjecting lengths of the roll to heat and pressure in molds to form rigid products.

18 Claims, 4 Drawing Sheets

(56) References Cited

U.S. PATENT DOCUMENTS

Figure 1:
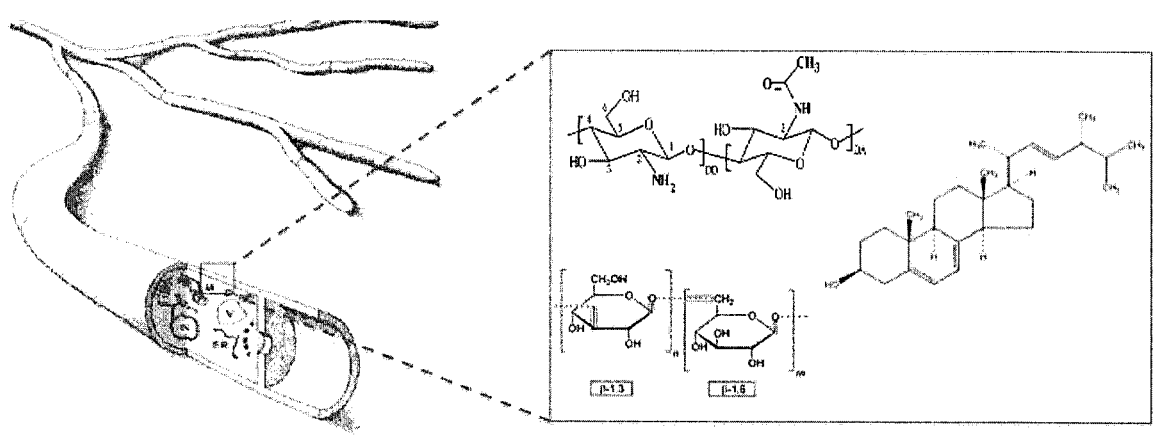

| | | |
|---|---|---|
| 3,421,554 A | 1/1969 | Carter |
| 3,477,558 A | 11/1969 | Fleischauer |
| 3,499,261 A | 3/1970 | Hullhorst et al. |
| 3,708,952 A | 1/1973 | Schulze et al. |
| 3,717,953 A | 2/1973 | Kuhn et al. |
| 3,782,033 A | 1/1974 | Hickerson |
| 3,810,327 A | 5/1974 | Giansante |
| 3,828,470 A | 8/1974 | Stoller |
| 3,885,048 A | 5/1975 | Liggett |
| 3,911,141 A | 10/1975 | Farr et al. |
| 3,961,938 A | 6/1976 | Iizuka et al. |
| 4,027,427 A | 6/1977 | Stoller et al. |
| 4,036,122 A | 7/1977 | Langen |
| 4,038,807 A | 8/1977 | Beardsley et al. |
| 4,063,383 A | 12/1977 | Green |
| 4,073,956 A | 2/1978 | Yates |
| 4,127,965 A | 12/1978 | Mee |
| 4,136,767 A | 1/1979 | Sarovich |
| 4,226,330 A | 10/1980 | Butler |
| 4,233,266 A | 11/1980 | Kummer |
| 4,263,744 A | 4/1981 | Stoller |
| 4,265,915 A | 5/1981 | MacLennan et al. |
| 4,294,929 A | 10/1981 | Solomons et al. |
| 4,337,594 A | 7/1982 | Hanacek et al. |
| 4,370,159 A | 1/1983 | Holtz |
| 4,568,520 A | 2/1986 | Ackermann et al. |
| 4,620,826 A | 11/1986 | Rubio et al. |
| 4,716,712 A | 1/1988 | Gill |
| 4,722,159 A | 2/1988 | Watanabe et al. |
| 4,878,312 A | 11/1989 | Shimizu |
| 4,922,650 A | 5/1990 | Akao et al. |
| 4,960,413 A | 10/1990 | Sagar et al. |
| 5,021,350 A | 6/1991 | Jung et al. |
| 5,030,425 A | 7/1991 | Bowers-Irons et al. |
| 5,074,959 A | 12/1991 | Yamanaka et al. |
| 5,085,998 A | 2/1992 | Lebron et al. |
| 5,088,860 A | 2/1992 | Stockdale et al. |
| 5,123,203 A | 6/1992 | Hiromoto |
| 5,230,430 A | 7/1993 | Kidder |
| 5,306,550 A | 4/1994 | Nishiyama et al. |
| 5,335,770 A | 8/1994 | Baker et al. |
| 5,370,714 A | 12/1994 | Ogawa |
| 5,433,061 A | 7/1995 | Hutchinson et al. |
| 5,440,860 A | 8/1995 | Meli et al. |
| 5,475,479 A | 12/1995 | Hatakeyama et al. |
| 5,498,384 A | 3/1996 | Volk et al. |
| 5,503,647 A | 4/1996 | Dahlberg et al. |
| 5,511,358 A | 4/1996 | Morita et al. |
| 5,532,217 A | 7/1996 | Silver et al. |
| 5,569,426 A | 10/1996 | Le Blanc |
| 5,589,390 A | 12/1996 | Higuchi et al. |
| 5,590,489 A | 1/1997 | Hattori et al. |
| 5,598,876 A | 2/1997 | Zanini et al. |
| 5,606,836 A | 3/1997 | Insalaco et al. |
| 5,647,180 A | 7/1997 | Billings et al. |
| 5,681,738 A | 10/1997 | Beelman et al. |
| 5,682,929 A | 11/1997 | Maginot et al. |
| 5,685,124 A | 11/1997 | Jandl |
| 5,711,353 A | 1/1998 | Ichikawa et al. |
| 5,802,763 A | 9/1998 | Milstein |
| 5,854,056 A | 12/1998 | Dschida |
| 5,888,803 A | 3/1999 | Starkey |
| 5,897,887 A | 4/1999 | Haeberli |
| 5,919,507 A | 6/1999 | Beelman et al. |
| 5,944,928 A | 8/1999 | Seidner |
| 5,948,674 A | 9/1999 | Mankiewicz |
| 5,979,109 A | 11/1999 | Sartor et al. |
| 6,041,544 A | 3/2000 | Kananen et al. |
| 6,041,835 A | 3/2000 | Price |
| 6,073,388 A | 6/2000 | Kananen et al. |
| 6,098,677 A | 8/2000 | Wegman et al. |
| 6,112,504 A | 9/2000 | McGregor et al. |
| 6,143,549 A | 11/2000 | Lamar et al. |
| 6,197,573 B1 | 3/2001 | Suryanarayan et al. |
| 6,226,962 B1 | 5/2001 | Eason et al. |
| 6,300,315 B1 | 10/2001 | Liu |
| 6,306,921 B1 | 10/2001 | Al Ghatta et al. |
| 6,329,185 B1 | 12/2001 | Kofod et al. |
| 6,349,988 B1 | 2/2002 | Foster et al. |
| 6,402,953 B1 | 6/2002 | Gorovoj et al. |
| 6,425,714 B1 | 7/2002 | Waddell |
| 6,444,437 B1 | 9/2002 | Sporleder et al. |
| 6,471,993 B1 | 10/2002 | Shastri et al. |
| 6,475,811 B1 | 11/2002 | Babcock |
| 6,482,942 B1 | 11/2002 | Vittori |
| 6,491,480 B2 | 12/2002 | Waddell |
| 6,500,476 B1 | 12/2002 | Martin et al. |
| 6,523,721 B1 | 2/2003 | Nomoto et al. |
| 6,603,054 B2 | 8/2003 | Chen et al. |
| 6,620,614 B1 | 9/2003 | Luth et al. |
| 6,660,164 B1 | 12/2003 | Stover |
| 6,679,301 B2 | 1/2004 | Makino et al. |
| 6,726,911 B1 | 4/2004 | Jülich et al. |
| 6,737,065 B2 | 5/2004 | Song et al. |
| 7,043,874 B2 | 5/2006 | Wasser et al. |
| 7,073,306 B1 | 7/2006 | Hagaman |
| 7,122,176 B2 | 10/2006 | Stamets |
| 7,179,356 B2 | 2/2007 | Aksay et al. |
| 7,395,643 B2 | 7/2008 | Franchini et al. |
| 7,514,248 B2 | 4/2009 | Gower et al. |
| 7,573,031 B2 | 8/2009 | Behar et al. |
| 7,621,300 B2 | 11/2009 | Bonney et al. |
| 7,661,248 B2 | 2/2010 | Conti et al. |
| 7,754,653 B2 | 7/2010 | Hintz |
| 7,836,921 B2 | 11/2010 | Isomura et al. |
| 8,001,719 B2 | 8/2011 | Bayer et al. |
| 8,067,237 B2 | 11/2011 | Mooney et al. |
| 8,205,646 B2 | 6/2012 | Isomura et al. |
| 8,227,224 B2 | 7/2012 | Kalisz et al. |
| 8,227,233 B2 | 7/2012 | Kalisz et al. |
| 8,241,415 B2 | 8/2012 | Wantling et al. |
| 8,298,809 B2 | 10/2012 | Kalisz et al. |
| 8,298,810 B2 | 10/2012 | Rocco et al. |
| 8,313,939 B2 | 11/2012 | Kalisz et al. |
| 8,517,064 B2 | 8/2013 | Isomura et al. |
| 8,658,407 B2 | 2/2014 | Lyons et al. |
| 8,763,653 B2 | 7/2014 | Weigel et al. |
| 8,999,687 B2 | 4/2015 | Bayer et al. |
| 9,068,171 B2 | 6/2015 | Kelly et al. |
| 9,079,978 B2 | 7/2015 | Räsänen et al. |
| 9,085,763 B2 | 7/2015 | Winiski et al. |
| 9,253,889 B2 | 2/2016 | Bayer et al. |
| 9,332,779 B2 | 5/2016 | Marga |
| 9,394,512 B2 | 7/2016 | Bayer et al. |
| 9,469,838 B2 | 10/2016 | Schaak et al. |
| 9,485,917 B2 | 11/2016 | Bayer et al. |
| 9,555,395 B2 | 1/2017 | Araldi et al. |
| 9,714,180 B2 | 7/2017 | McIntyre et al. |
| 9,752,122 B2 | 9/2017 | Marga et al. |
| 9,795,088 B2 | 10/2017 | Bayer et al. |
| 9,801,345 B2 | 10/2017 | Bayer et al. |
| 9,803,171 B2 | 10/2017 | Bayer et al. |
| 9,879,219 B2 | 1/2018 | McIntyre et al. |
| 9,914,906 B2 | 3/2018 | Winiski et al. |
| 10,125,347 B2 | 11/2018 | Winiski |
| 10,144,149 B2 | 12/2018 | Araldi et al. |
| 10,154,627 B2 | 12/2018 | McIntyre et al. |
| 10,172,301 B2 | 1/2019 | McNamara et al. |
| 10,266,695 B2 | 4/2019 | Lucht et al. |
| 10,407,675 B2 | 9/2019 | Bayer et al. |
| 10,525,662 B2 | 1/2020 | Bayer et al. |
| 10,533,155 B2 | 1/2020 | Kozubal et al. |
| 10,537,070 B2 | 1/2020 | Betts et al. |
| 10,575,579 B2 | 3/2020 | Egeland et al. |
| 10,577,579 B2 | 3/2020 | Kozubal et al. |
| 10,583,626 B2 | 3/2020 | Bayer et al. |
| 10,589,489 B2 | 3/2020 | Bayer et al. |
| 10,590,379 B2 | 3/2020 | Kozubal et al. |
| 10,687,482 B2 | 6/2020 | Ross et al. |
| 10,785,925 B2 | 9/2020 | McNamara et al. |
| 11,001,801 B2 | 5/2021 | Kozubal et al. |
| 11,015,168 B2 | 5/2021 | Kozubal et al. |
| 11,149,247 B2 | 10/2021 | Harney et al. |
| 11,261,420 B2 | 3/2022 | Kozubal et al. |

(56) References Cited

U.S. PATENT DOCUMENTS

| | | |
|---|---|---|
| 11,266,085 B2 | 3/2022 | Kaplan-Bie et al. |
| 11,272,726 B2 | 3/2022 | Macur et al. |
| 11,277,979 B2 | 3/2022 | Greetham et al. |
| 11,277,981 B2 | 3/2022 | Ross |
| 11,293,005 B2 | 4/2022 | Carlton et al. |
| 11,297,866 B2 | 4/2022 | Kozubal et al. |
| 11,343,979 B2 | 5/2022 | Mueller et al. |
| 11,359,074 B2 | 6/2022 | Kaplan-Bie et al. |
| 11,359,174 B2 | 6/2022 | Winiski et al. |
| 11,407,973 B2 | 8/2022 | Harney et al. |
| 11,420,366 B2 | 8/2022 | McIntyre et al. |
| 11,432,575 B2 | 9/2022 | Macur et al. |
| 11,459,541 B2 | 10/2022 | Harney et al. |
| 11,464,251 B2 | 10/2022 | Kozubal et al. |
| 11,466,245 B2 | 10/2022 | Harney et al. |
| 11,478,007 B2 | 10/2022 | Macur et al. |
| 11,505,779 B2 | 11/2022 | Kozubal et al. |
| 11,666,080 B2 | 6/2023 | Kozubal et al. |
| 2001/0012235 A1 | 8/2001 | Schuchardt |
| 2002/0110427 A1 | 8/2002 | Waddell |
| 2002/0131828 A1 | 9/2002 | Waddell |
| 2002/0131933 A1 | 9/2002 | Delmotte |
| 2003/0017565 A1 | 1/2003 | Echigo et al. |
| 2003/0056451 A1 | 3/2003 | Plsek et al. |
| 2003/0121201 A1 | 7/2003 | Dahlberg et al. |
| 2003/0157219 A1 | 8/2003 | Bijl et al. |
| 2003/0232895 A1 | 12/2003 | Omidian et al. |
| 2004/0000090 A1 | 1/2004 | Miller |
| 2004/0020553 A1 | 2/2004 | Amano |
| 2004/0166576 A1 | 8/2004 | Sadaie |
| 2004/0177585 A1 | 9/2004 | Vermette |
| 2004/0211721 A1 | 10/2004 | Stamets |
| 2005/0053778 A1 | 3/2005 | Hukkanen |
| 2005/0133536 A1 | 6/2005 | Kelsey et al. |
| 2005/0137272 A1 | 6/2005 | Gaserod et al. |
| 2006/0121006 A1 | 6/2006 | Chancellor et al. |
| 2006/0134265 A1 | 6/2006 | Beukes |
| 2006/0280753 A1 | 12/2006 | McNeary |
| 2007/0079944 A1 | 4/2007 | Amidon et al. |
| 2007/0196509 A1 | 8/2007 | Riman et al. |
| 2007/0225328 A1 | 9/2007 | Fritz et al. |
| 2007/0227063 A1 | 10/2007 | Dale et al. |
| 2007/0294939 A1 | 12/2007 | Spear et al. |
| 2008/0017272 A1 | 1/2008 | Isomura et al. |
| 2008/0046277 A1 | 2/2008 | Stamets |
| 2008/0047966 A1 | 2/2008 | Carson |
| 2008/0145577 A1 | 6/2008 | Bayer et al. |
| 2008/0234210 A1 | 9/2008 | Rijn et al. |
| 2008/0295399 A1 | 12/2008 | Kawai et al. |
| 2008/0296295 A1 | 12/2008 | Kords et al. |
| 2009/0107040 A1 | 4/2009 | Vandnhove |
| 2009/0111163 A1 | 4/2009 | Hoang et al. |
| 2009/0191289 A1 | 7/2009 | Lutz et al. |
| 2009/0241623 A1 | 10/2009 | Matano et al. |
| 2009/0246467 A1 | 10/2009 | Delantar |
| 2009/0272758 A1 | 11/2009 | Karwacki et al. |
| 2009/0307969 A1 | 12/2009 | Bayer et al. |
| 2009/0321975 A1 | 12/2009 | Schlummer |
| 2010/0101190 A1 | 4/2010 | Dillon |
| 2010/0158976 A1 | 6/2010 | O'Brien et al. |
| 2010/0159509 A1 | 6/2010 | Xu et al. |
| 2010/0199601 A1 | 8/2010 | Boldrini et al. |
| 2010/0227931 A1 | 9/2010 | Kuwano et al. |
| 2010/0243135 A1 | 9/2010 | Pepper et al. |
| 2010/0326564 A1 | 12/2010 | Isomura et al. |
| 2011/0094154 A1 | 4/2011 | Joaquin |
| 2011/0108158 A1 | 5/2011 | Huwiler et al. |
| 2011/0265688 A1 | 11/2011 | Kalisz et al. |
| 2011/0268980 A1 | 11/2011 | Kalisz et al. |
| 2011/0269209 A1 | 11/2011 | Rocco et al. |
| 2011/0269214 A1 | 11/2011 | Kalisz et al. |
| 2011/0306107 A1 | 12/2011 | Kalisz et al. |
| 2012/0000165 A1 | 1/2012 | Williams |
| 2012/0006446 A1 | 1/2012 | Isomura et al. |
| 2012/0060446 A1 | 3/2012 | Merz |
| 2012/0076895 A1 | 3/2012 | Kirejevas et al. |
| 2012/0115199 A1 | 5/2012 | Li et al. |
| 2012/0124839 A1 | 5/2012 | Kalisz et al. |
| 2012/0132314 A1 | 5/2012 | Weigel et al. |
| 2012/0135504 A1 | 5/2012 | Ross |
| 2012/0225471 A1 | 9/2012 | McIntyre et al. |
| 2012/0227899 A1 | 9/2012 | McIntyre et al. |
| 2012/0231140 A1 | 9/2012 | Hofmann et al. |
| 2012/0270031 A1 | 10/2012 | Guan et al. |
| 2012/0270302 A1 | 10/2012 | Bayer et al. |
| 2012/0315687 A1 | 12/2012 | Bayer et al. |
| 2013/0095560 A1 | 4/2013 | McIntyre et al. |
| 2013/0105036 A1 | 5/2013 | Smith et al. |
| 2013/0210327 A1* | 8/2013 | Corominas |
| 2013/0224840 A1* | 8/2013 | Bayer ............... B32B 5/02 435/254.1 |
| 2013/0274892 A1 | 10/2013 | Lelkes et al. |
| 2013/0309755 A1 | 11/2013 | McIntyre et al. |
| 2014/0038619 A1 | 2/2014 | Moulsley |
| 2014/0056653 A1 | 2/2014 | Scully et al. |
| 2014/0069004 A1 | 3/2014 | Bayer et al. |
| 2014/0093618 A1 | 4/2014 | Forgacs et al. |
| 2014/0120602 A1 | 5/2014 | Winiski et al. |
| 2014/0163142 A1 | 6/2014 | Zhang et al. |
| 2014/0173977 A1 | 6/2014 | Juscius |
| 2014/0186927 A1 | 7/2014 | Winiski et al. |
| 2014/0371352 A1 | 12/2014 | Dantin et al. |
| 2015/0033620 A1 | 2/2015 | Greetham et al. |
| 2015/0038619 A1 | 2/2015 | McIntyre et al. |
| 2015/0101509 A1 | 4/2015 | McIntyre et al. |
| 2015/0197358 A1 | 7/2015 | Larsen |
| 2015/0342138 A1 | 12/2015 | Bayer et al. |
| 2015/0342224 A1 | 12/2015 | Medoff |
| 2016/0002589 A1 | 1/2016 | Winiski |
| 2016/0073589 A1 | 3/2016 | McNamara et al. |
| 2016/0264926 A1 | 9/2016 | Winiski et al. |
| 2016/0355779 A1 | 12/2016 | Ross |
| 2017/0000040 A1 | 1/2017 | Bayer et al. |
| 2017/0028600 A1 | 2/2017 | McIntyre et al. |
| 2017/0071214 A1 | 3/2017 | Rehage |
| 2017/0218327 A1 | 8/2017 | Amstislavski et al. |
| 2017/0253849 A1 | 9/2017 | Miller et al. |
| 2017/0253852 A1 | 9/2017 | Bayer et al. |
| 2018/0014468 A1 | 1/2018 | Ross et al. |
| 2018/0148682 A1 | 5/2018 | Ross et al. |
| 2018/0282529 A1 | 10/2018 | Kaplan-Bie |
| 2018/0368337 A1 | 12/2018 | McIntyre et al. |
| 2019/0059431 A1 | 2/2019 | Kozubal et al. |
| 2019/0284307 A1 | 9/2019 | Chase et al. |
| 2019/0322997 A1 | 10/2019 | Schaak |
| 2019/0330668 A1 | 10/2019 | Kozubal et al. |
| 2019/0338240 A1 | 11/2019 | Carlton et al. |
| 2019/0357454 A1 | 11/2019 | Mueller et al. |
| 2019/0359931 A1 | 11/2019 | Mueller et al. |
| 2019/0390156 A1 | 12/2019 | Bayer et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0095535 A1 | 3/2020 | Kozubal et al. |
| 2020/0102530 A1 | 4/2020 | Winiski et al. |
| 2020/0146224 A1 | 5/2020 | Kaplan-Bie et al. |
| 2020/0157506 A1 | 5/2020 | Bayer et al. |
| 2020/0196541 A1 | 6/2020 | Ross et al. |
| 2020/0208097 A1 | 7/2020 | Winiski |
| 2020/0239830 A1 | 7/2020 | O'Brien et al. |
| 2020/0255794 A1 | 8/2020 | Amstislavski et al. |
| 2020/0268031 A1 | 8/2020 | Macur et al. |
| 2020/0270559 A1 | 8/2020 | Macur et al. |
| 2020/0392341 A1 | 12/2020 | Smith et al. |
| 2021/0017486 A1 | 1/2021 | Kozubal et al. |
| 2021/0127601 A9 | 5/2021 | Kaplan-Bie et al. |
| 2021/0317433 A9 | 10/2021 | Schaak |
| 2021/0348117 A9 | 11/2021 | Winiski |
| 2021/0401019 A1 | 12/2021 | Bayer et al. |
| 2022/0025318 A1 | 1/2022 | Gandia et al. |
| 2022/0142907 A1 | 5/2022 | Bayer et al. |
| 2022/0240557 A1 | 8/2022 | Kawabata et al. |
| 2022/0290199 A1 | 9/2022 | Greetham et al. |
| 2022/0295825 A1 | 9/2022 | Ghotra et al. |

(56) References Cited

U.S. PATENT DOCUMENTS

| | | |
|---|---|---|
| 2022/0298470 A1 | 9/2022 | Sayed et al. |
| 2022/0315881 A1 | 10/2022 | Macur |
| 2022/0333055 A1 | 10/2022 | Winiski et al. |
| 2022/0354068 A1 | 11/2022 | Carlton et al. |
| 2022/0354152 A1 | 11/2022 | Winiski et al. |
| 2022/0361424 A1 | 11/2022 | Mueller et al. |
| 2022/0386666 A1 | 12/2022 | Kawabata et al. |
| 2022/0396052 A9 | 12/2022 | Bayer et al. |
| 2023/0013465 A1 | 1/2023 | Kaplan-Bie et al. |
| 2023/0016412 A1 | 1/2023 | Perry |
| 2023/0024708 A1 | 1/2023 | Kaplan-Bie et al. |
| 2023/0056666 A1 | 2/2023 | Winiski et al. |
| 2023/0219265 A1 | 7/2023 | McIntyre et al. |

FOREIGN PATENT DOCUMENTS

| | | | |
|---|---|---|---|
| CN | 1358413 A | 7/2002 | |
| CN | 1732887 A | 2/2006 | |
| CN | 101248869 A | 8/2008 | |
| CN | 101653081 A | 2/2010 | |
| CN | 101743854 B | 2/2013 | |
| CN | 103146585 A | 6/2013 | |
| CN | 101892163 B | 7/2013 | |
| CN | 103283482 B | 7/2014 | |
| CN | 103396954 B | 11/2014 | |
| CN | 104025909 B | 5/2016 | |
| CN | 105961035 A | 9/2016 | |
| CN | 106380166 A | 2/2017 | |
| CN | 106635825 A | 5/2017 | |
| CN | 106947702 A | 7/2017 | |
| CN | 108249037 A | 7/2018 | |
| CN | 108753624 A | 11/2018 | |
| CN | 108934760 A | 12/2018 | |
| CN | 109897394 A | 6/2019 | |
| CN | 106613359 B | 1/2020 | |
| CN | 111066577 A | 4/2020 | |
| CN | 112225326 A | 1/2021 | |
| CN | 112442449 A | 3/2021 | |
| CN | 113501994 A | 10/2021 | |
| CN | 108753625 B | 11/2021 | |
| CN | 113692913 A | 11/2021 | |
| CN | 114175968 A | 3/2022 | |
| CN | 216106969 U | 3/2022 | |
| CN | 114617025 A | 6/2022 | |
| CN | 111990171 B | 7/2022 | |
| CN | 115104479 A | 9/2022 | |
| CN | 115181679 A | 10/2022 | |
| EP | 0226292 A1 | 6/1987 | |
| EP | 1312547 A1 | 5/2003 | |
| EP | 2677030 A1 | 12/2013 | |
| EP | 2735318 A1 | 5/2014 | |
| EP | 2835058 A1 | 2/2015 | |
| EP | 2875805 A1 | 5/2015 | |
| EP | 2878340 A1 | 6/2015 | |
| EP | 2485779 B1 | 2/2018 | |
| EP | 3292769 A1 | 3/2018 | |
| ES | 2497415 B1 | 4/2015 | |
| FR | 3006693 A1 | 12/2014 | |
| FR | 3071507 A1 | 3/2019 | |
| GB | 142800 A | 1/1921 | |
| GB | 1525484 A | 9/1978 | |
| GB | 2032456 A | 5/1980 | |
| GB | 2165865 A | 4/1986 | |
| IN | 358266 B | 7/2020 | |
| IN | 202111003691 A | 2/2021 | |
| IN | 202141024595 A | 7/2021 | |
| IN | 202031032279 A | 2/2022 | |
| JP | S52066679 A | 6/1977 | |
| JP | S55048388 A | 4/1980 | |
| JP | H03234889 A | 10/1991 | |
| JP | H049316 A | 1/1992 | |
| JP | 2002104988 A | 4/2002 | |
| JP | 2003526353 A | 9/2003 | |
| JP | 2009519042 A | 5/2009 | |
| JP | 2011130766 A | 7/2011 | |
| JP | 2016512699 A | 5/2016 | |
| JP | 6111510 B1 | 4/2017 | |
| JP | 2023002897 A | 1/2023 | |
| KR | 20050001175 A | 1/2005 | |
| KR | 101569282 B1 | 11/2015 | |
| KR | 101619664 B1 | 5/2016 | |
| KR | 101851655 B1 | 4/2018 | |
| KR | 102256335 B1 | 5/2021 | |
| KR | 1020220138955 A | 10/2022 | |
| KR | 102463058 B1 | 11/2022 | |
| KR | 1020220163083 A | 12/2022 | |
| KR | 1020220163084 A | 12/2022 | |
| MX | 2017016725 A | 6/2019 | |
| MY | 163845 A | 10/2017 | |
| RU | 2716106 C1 | 3/2020 | |
| WO | WO 1992/013960 | 8/1992 | |
| WO | WO 1998/052403 | 11/1998 | |
| WO | WO 1999/024555 | 5/1999 | |
| WO | WO 2001/087045 | 11/2001 | |
| WO | WO 2002/019798 | 3/2002 | |
| WO | WO 2003/089506 | 10/2003 | |
| WO | WO 2004/111181 | 12/2004 | |
| WO | WO 2005/023323 | 3/2005 | |
| WO | WO 2005/067977 | 7/2005 | |
| WO | WO 2007/031129 | 3/2007 | |
| WO | WO 2007/139321 | 12/2007 | |
| WO | WO 2008/025122 | 3/2008 | |
| WO | WO 2008/073489 | 6/2008 | |
| WO | WO 2010/005476 | 1/2010 | |
| WO | WO 2012/122092 | 9/2012 | |
| WO | WO 2012/148995 | 11/2012 | |
| WO | WO 2014/039938 | 3/2014 | |
| WO | WO 2014/110539 | 7/2014 | |
| WO | WO 2014/195641 | 12/2014 | |
| WO | WO-2014195641 A1 * | 12/2014 | ................ C08L 5/08 |
| WO | WO 2015/024751 | 2/2015 | |
| WO | WO 2016/149002 | 9/2016 | |
| WO | WO 2017/056059 | 4/2017 | |
| WO | WO 2017/120342 | 7/2017 | |
| WO | WO 2017/125602 A1 | 7/2017 | |
| WO | WO 2017/132523 | 8/2017 | |
| WO | WO 2017/136950 | 8/2017 | |
| WO | WO 2017/151684 | 9/2017 | |
| WO | WO 2017/205750 | 11/2017 | |
| WO | WO 2018/011805 | 1/2018 | |
| WO | WO 2018/014004 | 1/2018 | |
| WO | WO 2018/064968 | 4/2018 | |
| WO | WO 2018/183735 | 10/2018 | |
| WO | WO 2018/189738 | 10/2018 | |
| WO | WO 2019/046480 | 3/2019 | |
| WO | WO 2019/099474 | 5/2019 | |
| WO | WO 2019/178406 | 9/2019 | |
| WO | WO 2019/217175 | 11/2019 | |
| WO | WO 2019/226823 | 11/2019 | |
| WO | WO 2019/237059 | 12/2019 | |
| WO | WO 2019/246636 | 12/2019 | |
| WO | WO 2020/023450 | 1/2020 | |
| WO | WO 2020/072140 | 4/2020 | |
| WO | WO 2020/082043 | 4/2020 | |
| WO | WO 2020/082044 | 4/2020 | |
| WO | WO 2020/102552 | 5/2020 | |
| WO | WO 2020/106743 | 5/2020 | |
| WO | WO 2020/176758 | 9/2020 | |
| WO | WO 2020/186068 | 9/2020 | |
| WO | WO 2020/186169 | 9/2020 | |
| WO | WO 2020/237201 | 11/2020 | |
| WO | WO 2021/092051 | 5/2021 | |
| WO | WO 2021/144603 | 7/2021 | |
| WO | WO 2022/079452 | 4/2022 | |
| WO | WO 2022/091089 | 5/2022 | |
| WO | WO 2022/135757 | 6/2022 | |
| WO | WO 2022/157326 | 7/2022 | |
| WO | WO 2022/189600 | 9/2022 | |
| WO | WO 2022/195617 | 9/2022 | |
| WO | WO 2022/200049 | 9/2022 | |
| WO | WO 2022/212945 | 10/2022 | |
| WO | WO 2022/265498 | 12/2022 | |

OTHER PUBLICATIONS

(56) References Cited

OTHER PUBLICATIONS

Cha et al., "Biomimetic synthesis of ordered silica structures mediated by block copolypeptides". Nature (2000) 403(6767): 289-292.
Dugdale J. "This new surf company is making boards of mushrooms". Blog post—Jun. 25, 2015.
Halseide P., "Cutting brick the safe way". The Aberdeen Group (1988) Publication #M880354 in 2 pages.
Highland Woodworking, "Making Thin Lumber and Veneer Out of Ordinary Boards", Sales Website (2017) in 3 pages.
Holt et al., "Biobased Composition Boards Made from Cotton Gin and Guayule Wastes: Select Physical and Mechanical Properties", Int J Mater Prod Tech. (2009) 36: 104-114.
Islam et al., "Morphology and mechanics of fungal mycelium", Scientific Reports, (2017) 7(1): 1-12.
Kerem et al., "Chemically defined solid-state fermentation of Pleurotus Ostreatus". Enzyme Microbiol Tech. (1993) 15(9): 785-790.
Kokubo et al., "Ca,P-rich layer formed on high-strength bioactive glass-ceramic A-W". J Biomed Mater Res. (1990) 24(3): 331-343.
Koutsoukos et al., "Precipitation of calcium carbonate in aqueous solutions". J Chem Soc., Faraday Trans. 1, Physical Chemistry in Condensed Phases, (1984) 80(5): 1181-1192.
Lu et al., "Theoretical Analysis of Calcium Phosphate precipitation in simulated Body Fluid". Biomaterials (2005) 26(10): 1097-1108—Pre-Pub. Version by Hong Kong University of Science and Technology, Department of Mechanical Engineering, Kowloon; 34 pages.
Molvinger et al., "Porous chitosan-silica hybrid microspheres as a potential catalyst". Chem Mater. (2004) 16(17): 3367-3372.
Monmaturapoj et al., "Influence of preparation method on hydroxyapatite porous scaffolds". Bull Mater Sci. (2011) 34(7): 1733-1737.
Manoli et al., "Crystallization of calcite on chitin". J Cryst Growth, (1997) 182(1-2): 116-124.
Mushroom Source, "Aspen Wood Shavings for Mushroom Cultivation", Website (2015) in 2 pages.
National Institute of Health (NIH/NIBIB), "Tissue Engineering and Regenerative Medicine", Retrieved Sep. 24, 2018 from https://www.nibib.nih.gov/science-education/science-topics/tissue-engineering-and-regenerative-medicine in 13 pages.
Passauer U. et al., "Pilze in Hohlen" [Cave Mushrooms]. Denisia (2016) 37: 211-224.
Stewart B., "Concrete Fence Posts: Fact Sheet", Texas Agriculture Extension Service, Texas A & M University (1975) Article L-1368 in 4 pages.
Trinci et al., "II. Unrestricted Growth of Fungal Mycelia", The Mycota—Growth, Differenciation and Sexuality by Wessels et al. [Eds], Springer, Berlin, Heidelberg, (1994) Chapter II: 175-193.
Udawatte et al., "Solidification of xonotlite fibers with chitosan by hydrothermal hot pressing". J Mater Sci. Lttrs. (2000) 45(6): 298-301.
University of Sydney, "Competition Between Fungi". Webpage, accessed Jul. 16, 2014—http://bugs.bio.usyd.edu.au/learning/resources/Mycology/Ecology/competition.shtml in 3 pages.
Varma et al., "Porous calcium phosphate coating over phosphorylated chitosan film by a biomimetic method". Biomaterials (1999) 20(9): 879-884.
Wagner A. "Mycelium Biking—Eco-Design at its Best", Master's Thesis at Lulea University of Technology (2016) in 92 pages.
Woller R. "The Pearl Oyster Mushroom", University of Wisconsin Website (2011) in 2 pages.
Wan-Mohtar et al., "The morphology of Ganoderma lucidum mycelium in a repeated-batch fermentation for exopolysaccharide production", Biotechnology Reports (2016) 11: 2-11.
Weaver et al., "The stomatopod dactyl club: a formidable damage-tolerant biological hammer". Science (2012) 336(6086): 1275-1280.
Yamasaki et al., "A hydrothermal hot-pressing method: Apparatus and Application". J Mater Sci Lttrs. (1986) 5(3): 355-356.
Zivanovic et al., "Changes in Mushroom Texture and Cell Wall Composition Affected by Thermal Processing". J Food Service (2004) 69: 44-49.
Agnese et al., "Investigating the Influence of Various Plasticizers on the Properties of Isolated Films of Polyvinyl Acetat". The 37th Annual meeting and Exposition of the Controlled Release Society, Jul. 2010, Portland, OR U.S.A.
Amsellem et al., "Long-term preservation of viable mycelia of two mycoherbicidal organisms". Crop Protection (1999) 18: 643-649.
Angelini et al., "Effect of antimicrobial activity of Melaleuca alternifolia essential oil on antagonistic potential of Pleurotus species against Trichoderma harzianum in dual culture." World J Microbiol Biotech. (2008) 24(2): 197-202.
Antón et al., "PimM, a PAS Domain Positive Regulator of Pimaricin Biosynthesis in Streptomyces natalensis." Microbiol. (2007) 153: 3174-3183.
Appels et al., "Hydrophobin gene deletion and environmental growth conditions impact mechanical properties of mycelium by affecting the density of the material." Scientific Reports (2018) 8(1): 1-7.
Arshad et al., "Tissue engineering approaches to develop cultured meat from cells: a mini review." Cogent Food & Agriculture (2017) 3(1): 1320814 in 11 pages.
Ashiuchi et al., "Isolation of *Bacillus subtilis* (chungkookjang), a poly-gamma-glutamate producer with high genetic competence". Appl Microbiol Biotechnol. (2011) 57: 764-769.
Bajaj et al., "Poly (glutamic acid)—An emerging biopolymer of commercial interest". Bioresource Tech. (2011) 102(10): 5551-5561.
Baysal et al., "Cultivation of oyster mushroom on waste paper with some added supplementary materials". Biosource Technology (2003) 89: 95-97.
Begum et al., "Bioconversion and saccharification of some lignocellulosic wastes by Aspergillus oryzae ITCC-4857.01 for fermentable sugar production". Elect J Biotech. (2011) (14)5: 3 in 8 pages.
Belardinelli et al., "Actions of Adenosine and Isoproterenol on Isolated Mammalian Ventricular Myocytes." Circulation Res. (1983) 53(3): 287-297.
Belay et al., "Preparation and Characterization of Graphene-agar and Graphene Oxide-agar Composites." JOAPS (2017) 134(33): 45085.
Binder et al., "Phylogenetic and phylogenomic overview of the Polyporales". Mycologia (Nov. 12, 2013) 105(6): 1350-1373.
Blanchette et al., "Fungal mycelial mats used as textile by indigenous people of North America", Mycologia (Feb. 20, 2021) pp. 1-7.
Booth et al., "Potential of a dried mycelium formulation of an indigenous strain of Metarhizium anisopliae against subterranean pests of cranberry." Biocontrol Science and Technology (2000) 10: 659-668.
Bormann et al., "Characterization of a Novel, Antifungal, Chitin-binding Protein from Streptomyces Tendae Tü901 that Interferes with Growth Polarity." J Bacter. (1999) 181(24): 7421-7429.
Bowman et al., "The structure and synthesis of the fungal cell wall". Bioassays (2006) 28(8): 799-808.
Bružauskaite et al., "Scaffolds and Cells for Tissue Regernation: Different Scaffold Pore Sizes-Different Cell Effects." Cytotechnology (2016) 68(3): 355-369.
Byrd, "Clean meat's path to your dinner plate", The Good Food Institute, website accessed Nov. 14, 2018, https://www.gfi.org/clean-meats-path-to-commercialization; 11 pages.
Cerimi et al., "Fungi as source for new bio-based materials: a patent review", Fungal Biol Biotechnol. (2019) 6: 17; 10 pgs.
Chai et al., "β-Glucan Synthase Gene Overexpression and β-Glucans Overproduction in Pleurotus ostreatus Using Promoter Swapping". PLoS One (2013) 8(4): e61693 in 7 pages.
Chaudhary et al., "Understanding rice hull ash as fillers in polymers: a review". Silicon Chemistry (2002) 1:281-289.
Chi et al., "Can Co-culturing of Two White-rot Fungi Increase Lignin Degradation and the Production of Lignin-degrading Enzymes?" Inter'l Biodeter Biodegrad. (2007) 59(1): 32-39.

(56) References Cited

OTHER PUBLICATIONS

Collins English Dictionary, "Mould", retrieved from http://collinsdictionary.com/dictionary/english/mould, archived on Apr. 8, 2015, 3 pages.
Dias et al., "Synthesis and characterization of chitosan-polyvinyl alcohol-bioactive glass hybrid membranes". Biomatter (2011) 1(1): 114-119.
Elleuche et al., "Carbonic anhydrases in fungi". Microbiology (2010) 156: 23-29.
Elsacker et al., "Growing living and multifunctional mycelium composites for large-scale formwork applications using robotic abrasive wire-cutting", Construction Bldg Mater. (2021) 283: 122732 in 16 pages.
Fleet G.H., "Cell walls". in The Yeasts, by Rose et al. [Eds.] 2nd Edition. vol. 4. London: Academic Press. (1991) pp. 199-277.
Frandsen R.J.N., "A guide to binary vectors and strategies for targeted genome modification in fungi using Agrobacterium tumefaciens-mediated transformation". J Microbiol Methods (2011) 87: 247-262.
Gardening KnowHow, Perlite Soil Info: Learn About Perlite Potting Soil, online at www.gardeningknowhow.com/garden-how-to/soil-fertilizers/perlite-potting-soil.htm downloaded on Dec. 16, 2015., 3 pages.
Glowacki et al., "Bioconjugation of Hydrogen-bonded Organic Semiconductors with Functional Proteins." J Mate Chem. C (2015) 3(25): 6554-6564.
Goodell et al., "Fungal Decay of Wood: Soft Rot-Brown Rot-white Rot". In Development of Commercial Wood Preservatives; Schultz et al. [Ed.] ACS Symposium Series; American Chemical Society, Washington, D.C. (2008), Chapter 2, pp. 9-31.
Google Report, Complete colonization substrate mushroom (2 pages) Jan. 30, 2018., 2 pages.
Google Dictionary Definition "Composite", downloaded on Nov. 21, 2018; 1 page.
GOURMET Mushroom, Inc., "What is Mushroom?"—Mushroom Facts Mushroom Information—Educational & Science Projects (2004). Downloaded from www.gmushrooms.com, on Nov. 27, 2017; 5 pages.
Grant, James. J.—"An investigation of the airflow in mushroom growing structures, the development of an improved, three-dimensional solution technique for fluid flow and its evaluation for the modelling of mushroom growing structures", Doctoral Thesis Sep. 2002; 326 pages.
Greetham et al., "Pheotypic characterisation of Saccharomyces sensu stricto to InhibitoryCompounds Released During the Deconstruction of Lignocellulosic Material." 3th International Congress on Yeasts, ICY, Aug. 26-30, 2012 Madison, USA; 1 page.
Griffin et al., "Regulation of macromolecular synthesis, colony development and specificgrowth rate of Achlya bisexualis during balanced growth". J General Microbiol. (1974) 80(2): 381-388.
Growers Supply. "Horticultural Coarse Perlite—4 Cubic Fee—Growers Supply". URL: https://growerssupply.com; Growers Supply 2012; www.growerssupply.com/farm/supplies/prod1:gs_growing_mediums:pg111049.html; downloaded Dec. 14, 2020 in 3 pages.
Haneef et al., "Advanced Materials from Fungal Mycelium: Fabrication and Tuning of Physical Properties", Scientific Reports 7(1): 1-11; DOI: 10.1038/srep41292, Jan. 24, 2017.
Heinzkill et al., "Characterization of laccases and peroxidases from wood-rotting fungi (family Coprinaceae)." Appl Environ Microbiol. (1998) 64: 1601-1606.
Heisig et al., USGS, "Ground-Water Resources of the Clifton Park Area, Saratoga County, New York", 2002, retrieved from the internet (Oct. 15, 2016): http://ny.water.usgs.gov/pubs/wri/wri014104/wrir01-4104.pdf; 27 pages.
Home Depot "Miracle Gro® Perlite Mix", retrieved from the internet: http://homedepot.com/p/Miracle-Gro-8-pt-Perlite-Mix-74278430/204502291; 2 pages.
Home Depot "Pennington—Fast Acting Gypsum", retrieved from the internet: http://homedepot.com/p/Miracle-Gro-8-pt-Perlite-Mix-74278430/204502291; 2 pages.

Horton et al., "Regulation of Dikaryon-Expressed Genes by FRT1 in the Basidiomycete Schizophyllum commune". Fungal Genet Biol. (1999) 26(1): 33-47.
Howden et al., "The effects of breathing 5% CO2 on human cardiovascular responses and tolerance to orthostatic stress". Exper. Physiol. (2004) 89(4): 465-471.
Hüttner et al., "Recent advances in the intellectual property landscape of filamentous fungi", Fungal Biol Biotechnol. (2020) 7:16; 17 pgs.
Hyde et al., "The amazing potential of fungi: 50 ways we can exploit fungi industrially". Fungal Diversity (2019) 97(1): 1-136.
Instructables, How to Grow Oyster Mushroom Spawn (Low Tech), retrieved from the internet Aug. 19, 2018: http://www.instructables.com/id/1-How-to-Grow-Oyster-Mushroom-Spawn-Low-Tech/; 17 pages.
Jones et al., "Leather-like material biofabrication using fungi", Nature Sustainability (2020) https://doi.org/10.1038/s41893-020-00606-1, Sep. 7, 2020.
Kamzolkina et al., "Micromorphological features of *Pleurotus pulmonarius* (Fr.) Quel. and *P. ostreaturs* (Jacq.) P. Kumm. Strains in pure and binary culture with yeasts". Tsitologiia (2006) 48(2): 153-160.
Kemppainen et al., "Transformation of the Mycorrhizal Fungus Laccaria Bicolor using Agrobacterium tumefaciens." Bioengin Bugs (2011) 2(1): 38-44.
Kerem et al., "Effect of Mananese on Lignin Degradation by Pleurotus ostreatus during Solid-State Fermentation". Applied and Environmental Microbiology (1993) 59(12): 4115-4120.
Kilaru et al., "Investigating dominant selection markers for Coprinopsis cinerea: a carboxin resistance system and re-evaluation of hygromycin and phleomycin resistance vectors". Curr Genet. (2009) 55: 543-550.
Kim et al., "Current Technologies and Related Issues for Mushroom Transformation." Mycobiology (2015) 43(1): 1-8.
Kotlarewski et al., "Mechanical Properties of Papua New Guinea Balsa Wood." European J Wood Wood Products (2016) 74(1): 83-89.
Kück et al., "New tools for the genetic manipulation of filamentous fungi". Appl Microbiol Biotechnol. (2010) 86: 51-62.
Kües, U., "Life History and Development Processes in the Basidiomycete Coprinus Cinereus." Micro Molecular Biol Rev. (2000) 64(2): 316-353.
Kuhar et al., by Ingredi Potassium Sorbate vs Campden Tablets in Wine Making; Jun. 4, 2018. [online]; Retrieved from the Internet <URL: https://ingredi.com/blog/potassium-sorbate-vs-campden-tables-in-wine-making/>; 2 pages.
Kuo, 2005-2006. Glossary of Mycological Terms. Mushroom Expert. Com., pp. 1-13; downloaded from http://www.mushroomexpert.com/glossary.html (May 8, 2015).
Li et al., "Preparation and Characterization of Homogeneous Hydroxyapatite/Chitosan Composite Scaffolds via In-Situ Hydration". J Biomaterials Nanobiotech. (2010) 1: 42-49.
Luo et al., "Coprinus comatus: a basidiomycete fungus forms novel spiny structures and infects nematode." Mycologia (2004) 96(6): 1218-1225.
McPherson et al., "Dissolvable Antibiotic Beads in Treatment of Periprosthetic Joint Infection and Revision Arthroplasty: The Use of Synthetic Pure Calcium Sulfate (Stimulan®) Impregnated with Vancomycin & Tobramycin." Reconstructive Review (2013) 3(1) 12 pages.
Merriam-Webster, "Chamber" dictionary definition; https://www.merriam-webster.com/dictionary accessed Jul. 10, 2017; in 4 Pages.
Merriam-Webster, "pack" Thesaurus definition; https://www.merriam-webster.com/thesaurus; synonyms accessed Aug. 19, 2019; in 10 Pages.
Michielse et al., "Agrobacterium-mediated Transformation of the Filamentous Fungus Aspergillus Awamori." Nature Protocols (2008) 3(10): 1671-1678.
Mitchell et al., [Eds.] "Solid-State Fermentation Bioreactors." Springer Verlag, Berlin/Heidelberg (2006); TOC in 12 Pages.
Moore D., "Fungal Morphogenesis." Cambridge University Press, Cambridge, UK; (1998) TOC in 8 Pages.

(56) References Cited

OTHER PUBLICATIONS

Moore D., "Tolerance of Imprecision in Fungal Morphogenesis." In Proceedings of the 4th Meeting on the Genetics and Cellular Biology of Basidiomycetes (Mar. 1998) pp. 13-19.
Mushroom Growers' Handbook 1, "Oyster Mushroom Cultivation". Part II, Chapter 5, (2005) pp. 75-85.
Mushroom Growers' Handbook 2, "Shiitake Bag Cultivation", Part I Shiitake. Published by Mush World (2005) Chapter 4, pp. 73-90 and pp. 105-109.
Naknean et al., "Factors Affecting Retention and Release of Flavor Compounds in Food Carbohydrates." Inter'l Food Res J. (2010) 17(1): 23-34.
Newaz et al., "Characterization of Balsa Wood Mechanical Properties Required for Continuum Damage Mechanics Analysis." Proceedings of the Institution of Mechanical Engineers, Part L: Journal of Materials: Design and Applications (2016) 230(1): 206-218.
Norvell L., Fungi Biology. Encyclopedia.(2002); 2 pages.
Novoselova et al., "Cocultivation of Pleurotus ostreatus (Jacq.) P. Kumm. with yeasts". Moscow University Biol Sciences Bulletin (2011) 66(3): 102-105.
Nussinovitch "Polymer Macro-and Micro-Gel Beads: Fundamentals and Applications", DOI 10.1007/978-1-4419-6618_2, Springer Science & Business Media LLC (2010) TOC in 8 Pages.
Paz et al., "One Step Contruction of Agrobacterium-Recombination-ready-plasmids (OSCAR): An Efficient and Robust Tool for ATMT Based Gene Deletion Construction in Fungi." Fungal Gen Biol. (2011) 48(7): 677-684.
Peksen et al., "Favourable Culture Conditions for mycelial growth of Hydnum repandum, a medicinal mushroom." African Journal of Traditional, Complementary and Alternative Medicines (2013) 10(6): 431-434.
Peng et al., "Microbial biodegradation of polyaromatic hydrocarbons". FEMS Microbiol Rev. (2008) 32:927-955.
Perez et al., "Myxococcus xanthus induces actinorhodin overproduction and aerial mycelium formation by Streptomyces coelicolor." Microbial Biotech. (2011) 4(2): 175-183.
Philippoussis et al., "Production of Mushrooms Using Agro-Industrial Residues as Substrates", in Biotechnology for Agro-Industrial Residues, Chapter 9, (2009) pp. 163-187.
Poppe J., Mushroom Growers' Handbook 1, 2004, Part II. Chapter 5, "Substrate", pp. 80-81.
Pompei et al., "The Use of Olive Milling Waste-Water for the Culture of Mushrooms on Perlite". Acta Horticulturae (1994) 361:179-185.
Rai et al., "Production of Edible Fungi", in Fungal Biotechnology in Agricultural, Food, and Environmental Applications, D.K. Arora [Ed.], Marcel Dekker, Inc., (2003), Chapter 21, pp. 383-404.
Ross, P., "Pure Culture" 1997-Present; URL: <http://billhoss.phpwebhosting.com/ross/index.php?kind>; downloaded Dec. 14, 2016 in 11 pages.
Royse et al., "Influence of substrate wood-chip particle size on shiitake (Lentinula edodes) yield". Bioresource Tehnology (2001) 76(3): 229-233.
Sapak et al., "Effect of endophytic bacteria on growth and suppression of Tganoderma infection in oil palm". Int J Agric Biol. (2008) 10(2): 127-132.
Schaner et al., "Decellularized Vein as a Potential Scaffold for Vascular Tissue Engineering." J Vascular Surg. (2004) 40(1): 146-153.
Schirp et al., "Production and characterization of natural fiber-reinforced thermoplastic composites using wheat straw modified with the fungus Pleurotus ostreatus". J Appl. Polym Sci. (2006) 102: 5191-5201.
Scholtmeijer et al., "Effect of introns and AT-rich sequences on expression of the bacterial hygromycin B resistance gene in the basidiomycete Schizophyllum commune". Appl Environ Microbiol. (2001) 67(1): 481-483.
Schuurman J., "Unique agar Pearls." YouTube video; Feb. 16, 2012, <https://www.youtube.com/watch?v=8GqTTOHETPQ>; 1 page.
Science Daily, May 7, 2007, retrieved from the Internet; http://www.sciencedaily.com/releases/2007/05/070506085628.htm., 3 pages.
Seamon K.B., "Forskolin: Unique Diterpene Activator of Adenylate Cyclase in Membranes and in Intact Cells." PNAS (1981) 78(6): 3363-3367.
Sinotech et al., (2015): retrieved from the Internet http://www.sinotech.com/compressionAndTransferMolding.html., 4 pages.
Slater, M. "Young SoRo Entrepreneur Develops Environmentally Friendly Insulation." The Herald of Randolph. Jun. 21, 2007, pp. 1-2.
Staib et al., "Differential expression of the NRG1 repressor controls species-specific regulation of chlamydospore development in Candida albicans and Candida dubliniensis." Molecular Microbiol. (2005) 55(2): 637-652.
Stamets P., "Mycelium Running". Ten Speed Press (2005); pp. 18, 56, 58, 59, 85, 149, 157, 160 and 291 only.
Stamets P., "Growing Gourmet and Medicinal Mushrooms", (Undated) Chapter 21; p. 363.
Stanev et al., "Open Cell Metallic Porous Materials Obtained Through Space Holders. Part I: Production Methods, A Review". JMSE (2016) 139(5): 21 pages.
Stephens et al., "Bringing Cultured Meat to Market: Technical, Socio-political, and Regulatory Challenges in Cellular Agriculture." Trends in Food Science & Technology (2018) 78: 155-166.
Sundari et al., "Freeze-drying vegetative mycelium of Laccaria fraterna and its subsequent regeneration". Biotechnology Techniques (1999) 13: 491-495.
Tartar et al., "Differential expression of chitin synthase (CHS) and glucan synthase (FKS) genes correlates with the formation of a modified, thinner cell wall in in vivo-produced Beauveria bassiana cells." Mycopathologia (2005) 160(4): 303-314.
Téllez-Jurado et al., "Expression of a heterologous laccase by Aspergillus niger cultured by solid-state and submerged fermentations." Enzyme Microbial Tech. (2006) 38(5): 665-669.
Téllez-Téllez et al., "Growth and laccase production by Pleurotus ostreatus in submerged and solid-state fermentation." Appl Microbiol Biotechnol. (2008) 81(4): 675-679.
Thomas et al., "Growing Orchids in Perlite". In Perlite Plant Guide, The Schundler Company 1951, pp. 1-6, downloaded from http://www.schundler.com/index.html, archived on May 11, 2015.
TIMBERPRESS—"How Do Mushrooms Grow So Quickly.", downloaded from the internet: www.timberpress.com/blog/2017/01/how-do-mushrooms-grow-so-quickly, download Feb. 27, 2018 in 7 Pages.
Ugalde U., "Autoregulatory Signals in Mycelial Fungi" in The Mycota: A Comprehensive Treatise on Fungi as Experimental Systems for Basic and Applied Research. K. Esser [Ed.] Springer Publisher, 2nd Edition (2006) Chapter 11; pp. 203-213.
Universal Oil Field, "Sawdust", downloaded from universaloilfield.org on Aug. 23, 2018, 4 pages.
Vara et al., "Cloning and expression of a puromycin N-acetyl transferase gene from Streptomyces alboniger in Streptomyces lividans and Escherichia coli". Gene (1985) 33(22): 197-206.
Visser et al., "Pseudoxylaria as stowaway of the fungus-growing termite nest: Interaction asymmetry between Pseudoxylaria, Termitomyces and free-living relatives". Fungal Ecology (2011) 4(5): 322-332.
Volk (2003) "Tom Volk's Fungus of the Month for Oct. 1998". This month's fungus isPleurotus ostreatus; the Oyster mushroom, pp. 1-4, downloaded from http://botit.botany.wise.edu/toms_fungi/oct98.html on May 8, 2015.
Wang et al., "Influence of fungal elicitors on biosynthesis of natamycin by Streptomyces natalensis HW-2". Appl Microbiol Biothechnol. (2003) 97: 5527-5534.
Wikipedia, "Water gel (plain)", Wikipedia Contributors downloaded Aug. 21, 2017 in 1 Page.
Wikipedia, "Wood", downloaded on Nov. 26, 2018, 1 page.
Xiao et al., "A Water-soluble Core Material for Manufacturing Hollow Composite Sections." Comp. Structures (2017) 182: 380-390.
Yang et al., "Medicinal Mushroom Ganoderma lucidum as a Potent Elicitor in Production of t-Resveratrol and t-Peceatannol in Peanut Calluses". J Agric Food Chem. (2010) 58(17): 9518-9522.

(56) References Cited

OTHER PUBLICATIONS

Zadrazil et al., "Influence of CO2 Concentration on the Mycelium Growth of Three *Pleurotus* Species", European J. Appl. Microbiol., vol. 1, pp. 327-335 (1975).
Zimin et al., "The MaSuRCA genome assembler". Bioinformatics (2013) 29(21): 2669-2677.
International Search Report and Written Opinion for PCT/US2016/027698, mailed Aug. 10, 2016.
Abbadi et al., "Immunocytochemical identification and localization of lipase in cells of the mycelium of Penicillium cyclopium variety", Appl Microbial Biotechnol (1995) 42: 923-930.
Ando et al., "Cosmetic material for skin whitening—contains mushroom mycelium cultured matter and e.g. ginseng extract, chondroitin sodium sulphate and/or hyaluronic acid", WPI/Thomson (Jan. 14, 1992), 1992(8): Accession #1992-062018; Abstract of JP4009316A; in 9 pages.
Antinori et al., "Advanced mycelium materials as potential self-growing biomedical scaffolds." Scientific reports (2021) 11(1): 1-14.
Attias et al., "Biofabrication of Nanocellulose-Mycelium Hybrid Materials", Adv Sustainable Syst. (2020) 5(2): 2000196 in 12 pages; Supporting Information in 7 pages.
Borrás et al., "Trametes versicolor pellets production: Low-cost medium and scale-up", Biochem Eng J. (2008) 42(1): 61-66.
Collins English Dictionary, "Cavity", Definition; retrieved on Nov. 8, 2021; 1 page.
Green et al., "Mechanical Properties of Wood", Forest Products Laboratory, 1999. in Wood Handbook—Wood as an engineering material. Gen Tech. Rep. FPL-GTR-113, Chapter 4 in 46 pages.
Hidayat et al., "Characterization of polylactic acid (PLA)/kenaf composite degradation by immobilized mycelia of Pleurotus ostreatus". Inter Biodeter Biodegrad. (2012) 71: 50-54.
Holt et al. "Fungal mycelium and cotton plant materials in the manufacture of biodegradable molded packaging material: Evaluation study of select blends of cotton byproducts." J Biobased Mater Bioenergy (2012) 6(4): 431-439.
Jiang et al., "Manufacturing of Natural Composites with a Mycelium Binder and Vacuum-infused Vegetable Oil-based Resins", Poster dated May 2014; 1 page.
Jiang et al., "Vacuum Infusion of Mycelium-Bound Biocomposite Preforms with Natural Resins", CAMX ExpoConference Proceedings, Oct. 13-16, 2014, 13 pages.
Jiang et al., "Bioresin Infused then Cured Mycelium-based Sandwich-structure Biocomposites: ResinTransfer Molding (RTM) Process, Flexural Properties, and Simulation." J Cleaner Production (2019) 207: 123-135.
Jones et al., "Mycelim Composites: A Review of Engineering Characteristics and Growth Kinetics", J Bionanoscience (2017) 11(4): 241-257.
Jones et al., "Waste-derived Low-cost Mycelium Composite Construction Materials with Improved Fire Safety", FAM (Fire and Materials) (2018) 42(7): 816-825.
Jones et al., "Chitin-chitosan Thin Films from Microbiologically Upcycled Agricultural By-products. In 13th International Conference on the Mechanical Behavious of Materials, Melbourne, Australia (Jun. 2019) p. 66; in 7 pages.
Kuhn et al., [Eds.] Cell Walls and Membranes in Fungi—An Introduction (Abstract) in Biochemistry of Cell Walls and Membranes in Fungi, Chapter 1, Springer Verlag Berlin/Heidelberg 1990, 2 pages.
Merriam-Webster, "desiccated" (Adj.) Definition; downloaded on Nov. 8, 2021; 1 page.
Meyer et al., "Comparison of the Technical Performance of Leather, Artificial Leather, and Trendy Alternatives." Coatings (Feb. 2021) 11(2): 226; 14 pages.
Pathway-27, "Beta-glucan", Aug. 2012, retrieved from http://http://www.pathway27.eu/topstory/beta-glucan/ on Oct. 7, 2021 in 2 pages.

Vetchinkina et al., "Bioreduction of Gold (III) Ions from Hydrogen Tetrachloaurate . . . " Scientific Practical J Health Life Sciences No. 4, ISSN 22188-2268, (2013) pp. 51-56.
Wang et al., "Chemical and structural factors influencing enzymatic saccharification of wood from aspen, birch and spruce". Biomass Bioengin. (2018) 109: 125-134.
Williams, J. "Growth Industry", Financial Times Jan. 12, 2019 (Mogu—Radical by Nature); download from URL <: https://mogu.bio/growth-industry-financial-times-uk-article/> in 1 page.
Wosten et al., "How a fungus escapes the water to grow into the air", Current Biology. (1999) 9(2): 85-88.
Wösten et al., "Growing Fungi Structures in Space", ACT Research Category/Space Architecture; Noordwijk, The Netherlands (Oct. 15, 2018) in 17 pages.
Zeng Z., "Cosmetic composition for cleaning skin, comprises glossy ganoderma spores and collagens, content of glossy ganoderma spores in composition and content of collagens in composition", WPI/Thomson (Feb. 5, 2006) 7: Accession #2007-057767; Abstract of CN1732887A; in 11 pages.
Ziegler et al., "Evaluation of Physico-mechanical Properties of Mycelium Reinforced Green Biocomposites Made from Cellulosic Fibers", Appl Engin Agricult. (2016) 32(6): 931-938.
Britannica, The Editors of Encyclopaedia. "mold". Encyclopedia Britannica, Feb. 7, 2021, https://www.britannica.com/science/mold-fungus. 1 page.
Voronin et al., "Carbon and Nitrogen Isotope Composition of the Wood of Pinus sylvestris, Betula pendula and Populus tremula". Paleonotal J., Dec. 2020;54(8): 819-824.
Bandalan et al., "Inhibitory effect of garlic (*Allium sativum* L.) against bread mold and its influence on the quality of yeast-leavened bread", Int J Food Engineer. (Dec. 2018) 4(4): 256-262.
Bianchi et al., "Comparison between Allo-Kramer and Warner Bratzler Devices to Assess Rabbit Meat Tenderness", Italian J Animal Science (2007) 6(suppl): 749-751.
Boudaoud et al., "FibrilTool, an ImageJ plug-in to quantify fibrillar structures in rax microscopy images", Nature Protocols (2014) 9: 457-483.
Britannica, The Editors of Encyclopedia. "mold". Encyclopedia Britannica, Feb. 7, 2021, https://www.britannica.com/science/mold-fungus. 1 page.
Enrione et al., "Edible scaffolds based on non-mammalian biopolymers for Myoblast growth". Materials (Basel) (Dec. 2017) 10(12): 1404 in 15 pages.
Guan et al., "Construction and development of an auto-regulatory gene expression system in Bacillus subtilis". Microb Cell Fact Dec. 2015;14(1): 1-5.
Huang et al., "Genetically engineering Bacillus subtilis with a heat-resistant arsenite methyltransferase for bioremediation of arsenic-contaminated organic waste". Appl Enviro Microbiol. Oct. 1, 2015;81(19): 6718-6724.
Kim et al., "Effect of aeration and agitation on the production of mycelial biomass and exopolysaccharides in an enthomopahtogenic fungus Paecilomyces sinclairlii". Ltts Applied Microbiol. May 1, 2003;36(5): 321-326.
Kumla et al., "Cultivation of Mushrooms and Their Lignocellulolytic Enzyme Production Through the Utilization of Agro-Industrial Waste". Molecules Jun. 2020;25(12): 2811 in 41 pages.
Lumb et al., "Metal Chelating Tendencies of Glutamic and Aspartic Acids". J Phys Chem., Jul. 1953;57(7): 690-693.
Magyar C., "11 Smart uses for sawdust around your home & garden". Rural Sprout, published Oct. 26, 2020, 19 pages.
Miller R.K., "Quality Characteristics", in Muscle Foods: Meat Poultry and Seafood Technology, Kinsman et al. [eds], Springer Science & Media, (Mar. 2013) Chapter 11, 37 pages.
Mitcheson et al., "Cultured adult cardiac myocytes: Future applications, culture methods, morphological and electrophysiological properties". Cardiovasc Res. (1998) 39: 280-300.
OCDE—Organisation for Economic Co-operation and Development, Environment, Health and Safety Publications Series on the Safety of Novel Foods and Feeds, No. 26, Consensus Document on Compositional Considerations for New Varieties of Oyster Mushroom [*Pleurotus ostreatus*]: Key Food and Feed Nutrients, Antinutrients and Toxicants; Paris Nov. 2013, 42 pages.

(56) References Cited

OTHER PUBLICATIONS

Pacquette et al., "Simultaneous determination of chromium, selenium, and molybdenum in nutritional products by inductively coupled plasma/mass spectrometry: Single-laboratory validation", J of AOAC International (Jul. 2011) 94(4): 1240-1252.

Pang et al., "Facile fabrication of gradient density organic aerogel foams via density gradient centrifugation and UV curing in one-step", J Sol-Gel Sci Technol. (Nov. 2018) 85: 243-250.

Peter et al., "High Terpene Pines: Transforming existing and enabling new forest biorefineries". 2013; 1 page.

Phillips E., "Lignocellulose-degrading Microbes Give Plants New Life", American Soc Microb. (Mar. 25, 2022) 6 pages.

PubMLST (Public databases for Molecular Typing and Microbial Genome Diversity), "Isolate Bacillus Subtilis ATCC 6051", retrieved Sep. 15, 2022 from PubMLST; 1 page.

Roshita et al., "Effect of exposure to different colors light emitting diode on the yield and physical properties of grey and white oyster mushrooms", AIP Conference Proceedings (Nov. 2018) 2030(1): 020110 in 8 pages.

Sansinenea et al., "Secondary Metabolites of Soil *Bacillus* spp."; Biotechnol Lett. (2011) 33: 1523-1538.

Silverman J., "Development and Testing of Mycelium-based Composite Materials for Shoe Sole Applications." Thesis Spring 2018; Retrieved from the Internet: URL: http://udspace.udel.edu/bitstream/handle/19716/23768/Silverman_udel_006M_13300.pdf?sequence=1&isAllowed=y; (Apr. 1, 2018); 99 pages.

Tapias et al., Decellularized scaffolds as a platform for bioengineered organs, Curr Opin Organ Transplant (Apr. 2014) 19(2): 145-152.

Voronin et al., "Carbon and Nitrogen Isotope Composition of the Wood of Pinus sylvestris, Betula pendula and Populus tremula". Paleontological J., Dec. 2020;54(8): 819-824.

Wikipedia, "Soil". Downloaded on Sep. 14, 2022, 51 pages.

Wikipedia, "Compost". Downloaded on Sep. 14, 2022, 21 pages.

Yang et al., "Physical and mechanical properties of fungal mycelium-based biofoam", J Mater Civil Engin. (Jul. 2017) 29(7): 04017030 in 9 pages.

Zeigler et al., "The Origins of 168, W23, and other Bacillus subtilis Legacy Stains", J Bacter. (Nov. 2008) 190: 6983-6995.

ASTM International, "Standard Test Method for Tensile Properties of Plastics". Designation: D638-10, published Jun. 2010 in 16 pages.

Elsacker et al., "Mechanical, physical and chemical characterisation of mycelium-based composites with different types of lignocellulosic substrates". PLoS One. Jul. 22, 2019;14(7): e0213954 in 20 pages.

Elsoud et al., "Current trends in fungal biosynthesis of chitin and chitosan". Bull Nat'l Res Centre. Dec. 2019;43(1): 12 pages.

Fisher A., "Industrial-strength fungus—Densely packed rootlike fibers can do the job of Styrofoam, insulation and, yes, even bricks". TIME Feb. 8, 2010:1 page.

Hartl et al., "Fungal chitinases: diversity, mechanistic properties and biotechnological potential". Appl Microbiol Biotechnol. Jan. 2012;93: 533-543.

IFC Solutions. Natural Food Coloring. 2023; pp. 1-4.

INSIDER Business, "How Mushrooms are Turned into Bacon and Styrofoam—World Wide Waste", Apr. 11, 2021; XP093055859; Retrieved from the Internet: URL:https://www.youtube.com/watch?v=uznXI8wrdag&t=325s&ab_channel=InsiderBusiness [retrieved on Jun. 20, 2023] in 4 pages.

Kadirgamar S., "Company Uses Mushrooms to Grow Plastic Alternatives". Oct. 17, 2017; downloaded from https://daily.jstor.org/daily-author/skanda-kadirgamar/ in 5 pages.

Kumar, M.N.V.R., "A review of chitin and chitosan applications". React Function Polymers. Nov. 1, 2000;46(1):1-27.

MILLIPORE Sigma Database Search "Chelators", 2023, pp. 1-4.

Valencia et al., "Synthesis and application of scaffolds of chitosan-graphene oxide by the freeze-drying method for tissue regeneration". Molecules. Oct. 16, 2018;23(10): 2651 in 16 pages.

Wrona T., 10 Powerful Nutrients Found Only in Meat. Jun. 9, 2022. 20 pages.

\* cited by examiner

HIGH DENSITY RIGID MOLDED BODY OF COMPOSITE MYCOLOGICAL MATERIAL

This application claims the benefit of U.S. Provisional Patent Application No. 62/147,813, filed Apr. 15, 2015 and is a Division of U.S. Ser. No. 15/099,790 filed Apr. 15, 2016.

This invention relates to a high density rigid molded body of composite mycological material.

BACKGROUND

Published US Patent Application 2015/0101509 discloses a method of making a composite body employing chitin and glucan-containing mycelia cells and discrete particles wherein a mass of material made up of the chitin and glucan-containing mycelia cells and discrete particles is compressed under heat and compression for a time sufficient to allow cross-linking between the cellular matrix in the mycelia cells to bind the discrete particles together in the compressed body.

Generation of mycelial tissue throughout a woven, or non-woven lignocellulosic, saccharide, or synthetic matrix offers the ability to produce a uniform or non-uniform distribution of biomass that can be used for enhancing or targeting physical properties of a biological composite material prepared in a rolled format. Distribution of the fungal network provides a variety of intra or extracellular matrix components in fungal tissue that may act as a resin during a post-growth activation, or catalyzed process.

Compounds that are often associated with the fungal cell wall include chitin, chitosan, β-glucan, proteins, minerals, and other polysaccharides. When exposed to sufficient heat, moisture, or other catalyst, these have the potential to flow, contact, fuse and/or form covalent, physical, or ionic cross-links throughout the material.

A network of mycelial tissue proliferated across and throughout a fibrous, high flexibility or low-flexibility substrate, can be accessed or activated in a variety of ways to modify the physical characteristics of the fungal cell wall components and subsequently the bulk properties of the biomaterial. This practice proposes preparation, distribution, and activation pathways upon the extracellular (and/or intracellular) fungal cell saccharides, and other macro and micromolecular components.

OBJECTS OF THE INVENTION

It is an object of the invention to provide a high density rigid molded body of composite mycological material processed in a simple manner.

It is another object of the invention to provide a mycological composite in rolled format.

BRIEF SUMMARY OF THE INVENTION

Briefly, the invention provides a mycological composite material in the form of a web of mycelial tissue impregnated fibrous material characterized in being flexible and wherein the mycelial tissue contains chitin and glucan-containing mycelial cells.

In one embodiment, the mycological composite material is in the form of a roll with a web of porous material disposed in alternating layers the fibrous material.

In one embodiment, the method of producing the mycological composite material includes the steps of forming an inoculum of mycelial tissue; of inoculating a substrate of fibrous material with said inoculum; of rolling the inoculated substrate into a roll; and thereafter incubating the rolled inoculated substrate for a time sufficient for the mycelial tissue to grow hyphae that enmesh with the substrate by extending around the fibers of the substrate to form a cohesive unified filamentous network with the rolled inoculated substrate being characterized in being flexible.

The step of inoculating may be conducted by deposition of the inoculum on a surface of the substrate. For example, where the inoculum is in the form of solid particles, the inoculum is deposited under gravity onto the substrate of fibrous material and where the inoculum is in the form of a liquid, the inoculum is sprayed onto the substrate of fibrous material. In addition, the substrate may be conveyed in a continuous manner during deposition of the inoculum on the surface of the substrate.

Alternatively, the step of inoculating may be conducted by conveying the substrate of fibrous material through a bath of said inoculum.

After inoculation, the incubated substrate may be rolled up on itself or may be co-rolled with a support web of porous material into a composite roll of alternating layers (or convolutions) of substrate and porous material. Thereafter, the composite roll is dehydrated to below 20% moisture and ideally below 8% for storage and/or transportation to another site for further processing. In this condition, the incubated substrate. is flexible.

The term "flexible" means that the rolled substrate may be unrolled, for example, into a flat web or sheet while retaining the integrity of the incubated substrate.

In accordance with the invention, the mycelial tissue of the inoculum contains chitin and glucan-containing mycelial cells. Thus, in order to further process the rolled inoculated substrate, a length of the incubated substrate is unrolled from the rolled substrate and subjected to heat and pressure sufficient to cause the glucan-containing mycelial cells therein to bond said length into a rigid structure.

In order to prepare the composite roll of alternating layers of substrate and porous material, a flow of moisture is passed through the layers of porous material into the layers of substrate to re-hydrate the layers of substrate to between 30% and 70% moisture.

Alternatively, where a length of the incubated substrate is unrolled from the rolled substrate and subjected to heat and pressure, a flow of steam may be passed through the layers of porous material into the layers of substrate to re-hydrate the layers of substrate.

The method described here can be applied to any species of fungi and tailored to yield the desired extent, or combination of modifications thereof.

Figure 2:
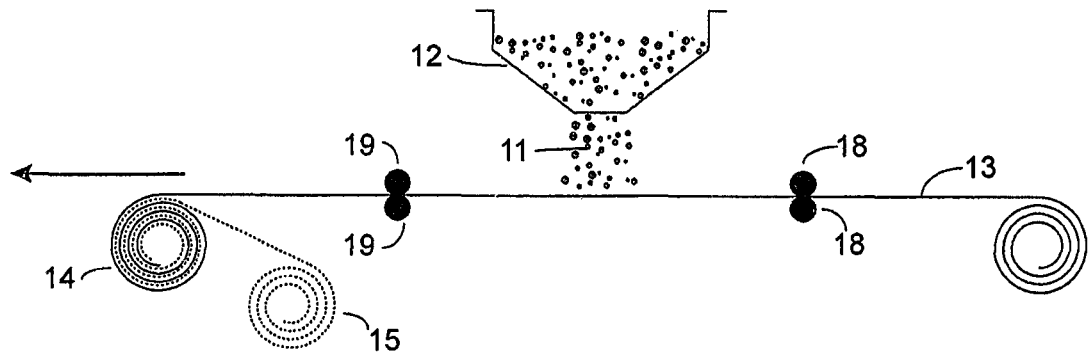
Figure 3:
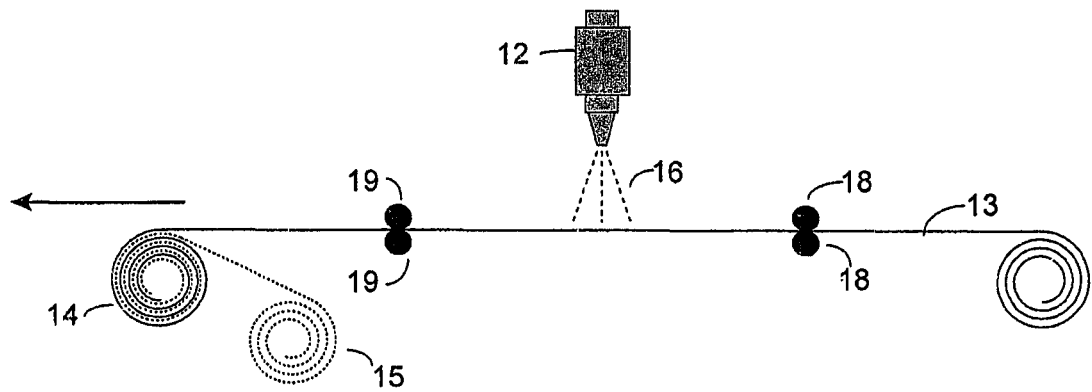
Figure 4:
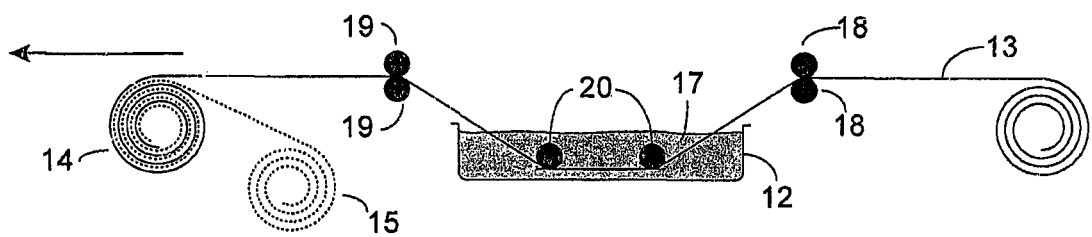
Figure 5:
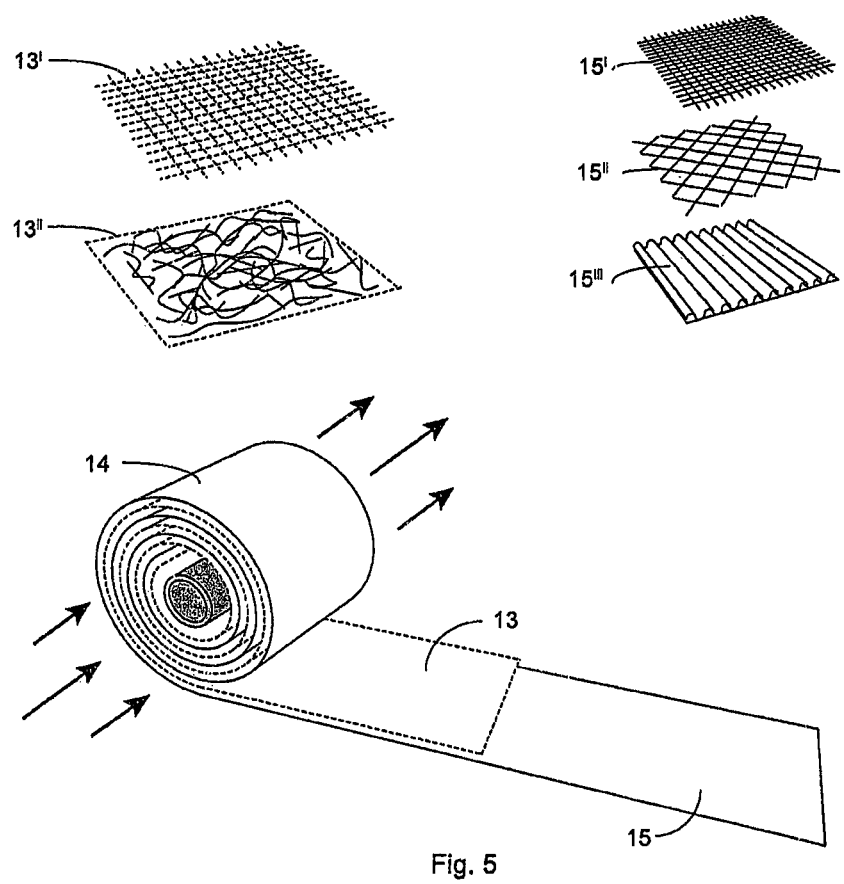
Figure 6:
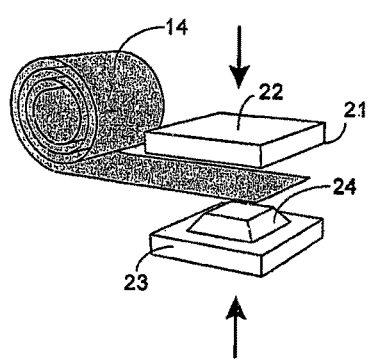
Figure 7:
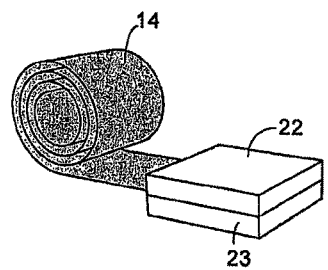
Figure 8:
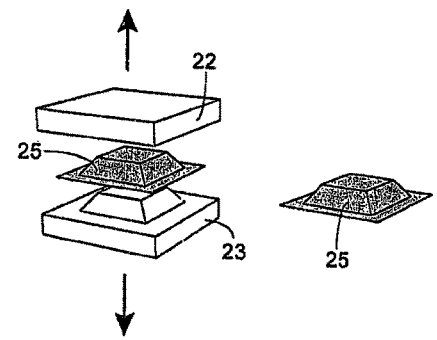
Figure 9:

These and other objects and advantages of the invention will become more apparent form the following detailed description taken in conjunction with the accompanying drawings wherein:

FIG. 1 illustrates an image of a fungal cell wall and a deconstructed section of the cell wall with intracellular chitin and structural saccharides;

FIG. 2 schematically illustrates an apparatus for depositing an inoculum under gravity onto a travelling web of fibrous substrate in accordance with the invention;

FIG. 3 schematically illustrates an apparatus for depositing an inoculum by spraying onto a travelling web of fibrous substrate in accordance with the invention;

FIG. 4 schematically illustrates an apparatus for passing a travelling web of fibrous substrate through a bath of inoculum in accordance with the invention;

FIG. 5 schematically illustrates a flexible mycological composite material produced in accordance with the invention in a partially unrolled condition; and FIG. 6 schematically illustrates an initial step in a heat and compression process during the further processing of the mycological composite material of FIG. 5;

FIG. 7 schematically illustrates the mycological composite material of FIG. 5 in a heated form during a heat and compression step in accordance with the invention;

FIG. 8 schematically illustrates the mycological composite material of FIG. 5 during removal from the form of FIG. 7; an FIG. 9 illustrates a formed mycelium/substrate product formed in the form of FIG. 7.

FIG. 1 illustrates an image of part of a fungal network of hyphae 10 with a detail of the structure of a fungal cell wall composed of intracellular chitin and structural saccharides shown to the right.

As illustrated in the detail at Right, top, the fungal cell wall has repeat units of the structural polymer chitin, and the deacetylated derivative, chitosan, where the degree of deacetylation (DD), and degree of acetylation (DA) can vary as complimentary fractions between 0-1. As illustrated in the detail at Right, middle, the fungal cell wall has structural sterol commonly found in fungal cell membranes and as illustrated in the detail at Right, bottom the fungal cell wall has repeat units of the structural saccharides β-d (1,3) and (1,6) glucans. Not shown: catechols, hydrophobins, proteins or other more complex structural cell components.

Referring to FIG. 2, the process for the production of mycelial composite surfaces in a roll-to-roll format is performed in accordance with the following steps that can be used alone or in combinations thereof.

First, an inoculum 11 of mycelial tissue is provided at an inoculation station 12. For example, the inoculum 11 may be obtained by growing a growth media as a solid mass which is then ground up to produce particles or pellets with mycelium therein as disclosed in US 2015/0101509.

Second, a substrate of fibrous material 13 is passed under the inoculation station 12 as a travelling web with the inoculum 11 being deposited under gravity onto the surface of the web 13.

Third, the inoculated substrate 13 is rolled into a roll 14 and thereafter incubated for a time sufficient for the mycelial tissue to grow hyphae that enmesh with the substrate by extending around the fibers of the substrate to form a cohesive unified filamentous network with the rolled inoculated substrate being characterized in being flexible.

Alternatively, the incubated substrate 13 may be rolled up with a support web of porous material 15 into a roll of alternating layers of substrate and porous material.

Fourth, in either case, the roll 14 is dehydrated to below 20% moisture and ideally below 8% for storage and/or transportation to another site for further processing. In this condition, the incubated substrate 13. is flexible.

Referring to FIG. 3, wherein like reference characters indicate like parts as above, the process of FIG. 2 may be modified by employing a liquid inoculum spray 16 in the inoculation station 12 for deposition of the inoculum 16 on a surface of the substrate 13.

Referring to FIG. 4, wherein like reference characters indicate like parts as above, the process of FIG. 2 may be modified by employing a bath of inoculum 17 in the inoculation station 12 for passage of the web of substrate 13 therethrough.

As indicated in FIG. 3, pairs of rollers 18, 19 are provided for conveying the web of substrate 13 through the inoculation station 12, preferably under a slight tension, and guide rollers 20 are provided for guiding the substrate 13 through the bath of inoculum.

Referring to FIG. 5, the substrate of fibrous material 13 may be selected from a woven substrate 13' or a non-woven substrate 13" and, where used, the support web of porous material 15 may be selected form a plastic porous membrane 15', a plastic mesh or similar 15" and a plastic corrugate or similar 15'''.

The particulars of the process steps are as follows:
1. Substrate selection, use one or more of the following materials, in combination or concert, as substrate or additional material to existing myceliated material: 1 grams/square meter to 100 kg/square meter of fibrous material deemed appropriate:
    a. Flexible agricultural waste fibers
    b. Non-flexible agricultural fibers
    c. Lignocellulosic fibers
    d. Sugar fibers
    e. Cellulosic fibers
    f. Lignin fibers
    g. Hemicellulose (fibrous form)
    h. Xylose (fibrous form)
    i. Electrospun cellulosic or lignocellulosic fibers
    j. Electrospun cellulosic or lignocellulosic fibers on a synthetic support
    k. Solvent (and/or salt) spun or extracted cellulosic or lignocellulosic fibers
    l. Solvent (and/or salt) spun or extracted cellulosic or lignocellulosic fibers on a synthetic support
    m. Non-woven lignocellulosic fibers on a synthetic support
    n. Woven lignocellulosic fibers on/in a lignocellulosic support
    o. Lignocellulosic fibers woven into synthetic support
    p. Entangled lignocellulosic fibers (Hydro, needle-punched, or other mechanical process) fibers on synthetic or natural fiber or particle support
    q. Combination of the like
2. Prepare Substrate material for inoculation using one or more of the following:
    a. Steam
    b. Heat
    c. Pressure
    d. $H_2O_2$
    e. Acid sterilization
    f. Base sterilization
    g. UV/Ebeam
    h. Boiled (roll to roll or batch autoclaved)
    i. PEO sterilized (e.g. cinnemaldehyde)
    j. Co-habitation with other species, or spores
    k. Pre-digested by other organisms
    l. No preparation used, i.e. raw
    m. Combination of the like
3. Use one or more of the following inoculation media or methods to introduce organism binder to mat/fibrous material in order to generate biological resin.
    a. Pre-inoculated, unaltered grain/millet spawn particle form distributed onto substrate by deposition or conveyance
    b. Pre-inoculated grain/millet spawn particle in altered size/aspect ratio by mechanical process, distributed onto substrate by deposition or conveyance
    c. Pre-inoculated grain/millet spawn particle in altered size/aspect ratio by mechanical process, filtered and distributed onto substrate by deposition or conveyance d. Fibrous substrate grown in contact with surface of adjacent pre-inoculated material
  e. Suspended/distributed tissue, cultured and placed onto substrate without co-conveyance of pre-inoculated material.
  f. Ground fibers or particulates pre-inoculated with mycelium to form a batting during incubation
  g. Spores (sexual or asexual, cohabitating or compatible) or suspended spores
  h. Combination of reproductive and vegetative mycelial tissue distributed onto substrate by deposition or conveyance
  i. Spores and/or tissue with added nutrition, in solution or solid form.
  j. Ground fibers or particulates pre-inoculated with mycelium to form a batting during incubation.

Nutrition may be added as an option with the amount of added nutrition ranging from no additive (0 g) to 25% by mass of substrate mat or pre-matted fiber/particle) material. If added, the nutrition may be selected from:
  i. Grain, flours, minerals, starches, proteins
    a. Clear flour
    b. maltodextrin
    c. Wheat bran
    d. Algae
    e. Yeast
  ii. Nutrition can be liquid and/or suspension (dilute to semi-dilute regime)
  iii. Nutrition can be paste (ranging from Newtonian fluid, viscous suspension, semi-dilute suspension, concentrated suspension, viscoelastic paste, gel)
    1. No additive
    2. Liquid with additive (natural or synthetic)
      a. Starch, viscosity agent, gelling agent,
    3. Solids diluted or suspended
  k. Combination of the like
4. Mycelial tissue growth to obtain desired biomass content. Use one or the following in combination or concert with the method described in U.S. Pat. No. 8,001,719 for producing rapidly renewable chitinous material.
  a. Incubate
    i. Parameters including, but not limited to:
      1. Temperature (5 C-40 C)
      2. Relative Humidity (10%-100%)
      3. CO2 (0%-20%)
    ii. Physical format
      1. Roll substrate and biomass prior to incubation
        a. Stand-off using synthetic or natural material as a mechanically stable support for substrate material to grow upon in a rolled format, minimizing dimensional instability during colonization (incubation) period
        b. Corrugated sheeting rolled goods
        c. Non-corrugated sheeting
        d. Woven fabrics
        e. Perforated sheeting
        f. Rods/wires/mesh
        g. Screen materials
        h. Combination of the like
        i. Actively aerated
        j. Passively aerated
      2. Sheets, non rolled configuration of 1 above
      3. Lamination: Allow fungal tissue to grow and penetrate into/from:
        a. Adjacent mat material
        b. Adjacent particulate material
        c. Synthetic material
        d. Material with competing/cohabitating organism
    iii. Preconfigured shape
      1. Preformed in dimensions near net to final product dimensions
      2. As predetermined shape optimal for pressing/rolling/dehydrating/shipping Referring to FIGS. 6 to 9, in order to process the roll 14 of inoculated substrate into a final product, use is made of a heat and compression apparatus 21, such as described in US 2015/0101509.

As indicated in FIG. 5, a length of the incubated substrate is unrolled from the rolled substrate 14 and placed between two mold forms 22, 23 of the apparatus 21. The lower mold form 23 has a protrusion 24 and the upper mold form 22 has a mating cavity (not shown) in order to form the substrate into a desired shape.

Thereafter, as indicated in FIG. 6, the mold forms 22, 23 are closed on the length of substrate 14 and the substrate 14 is subjected to heat and pressure sufficient to cause the glucan-containing mycelial cells therein to bond the length into a rigid structure 25 as indicated in FIG. 8.

After opening of the mold forms 22, 23 from each other as indicated in FIG. 8, the rigid structure 25 which conforms to the shape of the mold cavity of the apparatus 21 is removed.

As indicated in FIG. 9, the rigid body 25 is of a rectangular shape with a truncated trapezoidal projection and has a thickness that may be uniform throughout depending on the clearances between the mold forms 22, 23.

The particulars of the process steps for processing of the inoculated substrate roll 14 are as follows:
  5. Dehydrate proliferated mycelial/lignocellulosic material, if necessary or desired, to below 20% moisture by mass and ideally below 8%.
    a. Rehydrate up to 30% to 70% moisture depending on substrate to re-animate tissue
      i. Follow desired (or combination) of curing steps in section 6
    b. Steam during pressing to activate glucans and other intra/extracellular compounds:
      i. Use existing channels in platen
      ii. Introduce a hydrated layer to fuse
      iii. Introduce a hydrated layer to be delaminated
      iv. Use high, or low vapor pressure solvents to control vapor release
      v. Use chemical agents to deteriorate or enhance physical crosslinking
      vi. Use a biomimecry process to induce mineralization or other naturally occurring process
        1. Use heat/agitation/energy source or pressure to accelerate (or decelerate chemical or biological process)
        2. Use cold or heat transfer to control thermodynamics and kinetics
      vii. Use a second, third, or subsequent organism to enhance network fusing through delivered exudate, or vapor
  6. Select one or more of the following methods of curing (or the like) to the fungal colonized, uncolonized, or colonized and dehydrated mat material
    a. Non-heated compression (e.g. compacting)
    b. Heated (25 C-2000 C)
    c. Pressing flat (0.1-1,000,000 psi)
      i. Single open-press
      ii. Multi open-press iii. Continuous press
iv. Roller press
v. Stretching/alignment roller apparatus
vi. Cooling/treating bath
vii. Pullout assembly
viii. Reheating stations
ix. Integrated (or non-integrated) cutting unit
x. Integrated coating (pre, or post-curing) of natural or synthetic material to enhance stiffness, flame retardance, antimicrobial, abrasion
d. Pressing on feature-containing surface (0.1-1,000,000 psi)
e. Heated pressing flat (0.1-1,000,000 psi)
f. Heated pressing on feature-containing surface (0.1-1,000,000 psi)
g. Embossed (heated or non-heated)
h. Roll to roll drying
i. Spray coating prior to pressing
  i. Enhance/attenuate adhesion, internal bond strength antimicrobial activity, abrasion resistance, surface finish, modulus, or other like properties
j. Injected components (solvent, chemical, or the like)
  i. Enhance/attenuate adhesion, internal bond strength, antimicrobial activity, abrasion resistance, surface finish, modulus, or other like properties
k. Plant essential oils
l. Dehydrate
m. Ebeam/UV/radiation
n. Combination of the like
7. Select one or more of the following feature containing surfaces (or the like) for transferring features to inoculated mat material (cured, or non-cured) [GT=>add as parallel to flow-chart, e.g. bottle type process]
a. Isobaric transfer of features (constant pressure)
b. Isochoric transfer (strain controlled)
c. Incremental pressing,
d. Embossed features
e. Roll-to-roll die cutting
f. Curved surface on single or multi-open press
g. Flat or curved surface with cutouts stamped into
h. Combination of the like It should be noted that all chemical modifications (naturally, synthetically, or enzymatically derived) may be executed in variant levels of functionality (i.e. substitutions may range from 0 to 1 to 2 or higher), e.g. bifunctional or higher to involve reactive steps intra or inter-cellular biomolecule chain linking to impart targeted chemical modification characteristics, and additionally effect network structure and performance, and subsequently bulk material properties.

The following is an example of making a rolled composite in accordance with the invention.

Example: Preparation of Inoculated Hemp Mat Material Using a Grain Spawn Slurry Inoculum 1. Aseptically, combine grain spawn in a blended with sterile water at a rate of 2:1
2. Blend material for 90 seconds until the grains have been mechanically disrupted and have the appearance of a paste ("inoculum concentrate")
3. In an aseptic vessel of sufficient size: Adjust the volume of inoculum concentrate with additional sterile water to yield the desired quantity and inoculation rate. Additional nutrients as described in the above list (flour, wheat bran, etc.) may also be mixed in at this step. This process yields a bath of "working inoculum".
4. Introduce a sanitized (via a 60 min soak in 10% hydrogen peroxide) hemp mat material into the bath of working inoculum using a set of rollers to remove excess residual hydrogen peroxide.
5. Once mat has had as little as 2-10 seconds of dwell time in the inoculum bath, the mat is removed by being passed through a second set of sanitary rollers. These rollers remove the excess inoculum liquid, which may be reclaimed for further processing. (note: in practice, this brief dwell time may be regarded as a continuous passing of mat through the inoculum bath.)
6. As the mat is conveyed out of the bath and through the rollers, the may be rolled continuously onto a spool of rigid plastic or other solid support. To do this efficiently, this process is executed synchronously with a solid support being unrolled to form a "roll to roll" product.
7. The completed roll of material is placed in a suitable incubation environment to maintain temperature and RH amenable to the organism with which the material was inoculated for the duration of growth.
8. The fully colonized mat (on the order of 4-20 days of incubation, highly dependent on the species, substrate, and nutrition used) may be stored.
9. Completed mat may be dried and dehydrated to use in a low-density format. The completed mat may also be processed with heat and pressure to yield a higher density rigid biocomposite.

The invention thus provides a relatively simple process for the production of mycelial composite surfaces in a roll-to-roll format as well as a mycological composite in rolled format.

The invention further provides a mycological composite in rolled forma that can be unrolled and subjected to heat and pressure to make rigid mycological products.

What is claimed is:

1. A process for forming a unified filamentous network of mycological material, comprising:
   providing a mycological material comprising mycelial tissue of a filamentous fungus enmeshed in a support web of porous material, wherein the support web of porous material contacts the mycelial tissue in alternating layers;
   obtaining a length of the mycological material; and
   molding the length of mycological material with sufficient heat and pressure to bond the mycological material and to shape the mycological material into a preconfigured shape.

2. The process of claim 1, wherein the mycelial tissue comprises hyphae enmeshed in the support web of porous material, further comprising:
   contacting the support web of porous material with a substrate such as to form a plurality of alternating layers of the mycelial tissue and the support web of porous material, wherein the support web of porous material comprises a plurality of fibers.

3. The process of claim 2, wherein the plurality of fibers comprises woven fibers.

4. The process of claim 2, wherein the plurality of fibers comprises non-woven fibers.

5. The process of claim 2, wherein the plurality of fibers is selected from the group consisting of: cellulosic fibers and synthetic fibers.

6. The process of claim 2, wherein the hyphae extend around the plurality of fibers.

7. The process of claim 1, wherein the mycological material comprises a substrate comprising a plurality of fibers, the mycelial tissue comprising hyphae that extend through and enmesh in the support web of porous material.

8. The process of claim 7, wherein the support web of porous material comprises a synthetic material.

9. The process of claim 7, wherein the support web of porous material comprises a plastic material.

10. The process of claim 9, wherein the support web of porous material comprises a plastic mesh.

11. The process of claim 1, wherein molding the length of mycological material with sufficient heat and pressure comprises applying heat to the mycological material at a temperature of between 25° C. and 2000° C.

12. The process of claim 1, wherein molding the length of mycological material with sufficient heat and pressure comprises applying pressure to the mycological material at a pressure of between 0.1 pounds per square inch and 1000 pounds per square inch.

13. The process of claim 1, further comprising:
positioning the length of the mycological material on a mold form,
and wherein molding the length of mycological material with sufficient heat and pressure comprises applying heat and pressure such that the mycological material has a shape that conforms to the mold form.

14. The process of claim 1, further comprising:
positioning the length of the mycological material on a flat surface, wherein molding the length of mycological material with sufficient heat and pressure comprises applying heat and pressure using a heated press to form a high density rigid molded sheet of mycological material.

15. The process of claim 1, wherein the mycological material comprises a water content, and wherein providing the mycological material comprises:
dehydrating the mycological material such that the water content of the mycological material is less than 20% water by mass.

16. The process of claim 1, wherein the mycelial tissue comprises chitin and glucan-containing mycelial cells.

17. The process of claim 16, wherein molding the length of mycological material with sufficient heat and pressure further comprises applying steam to activate the glucan within the mycelial tissue to form crosslinking between the chitin and glucan throughout the mycological material.

18. The process of claim 1, further comprising:
(a) selecting a substrate for inoculation with the filamentous fungus; (b) inoculating the substrate with the filamentous fungus;
(c) contacting the substrate with the support web of porous material;
(d) incubating the substrate such that the filamentous fungus colonizes the substrate and enmeshes with the support web of porous material;
(e) repeating steps (b)-(d) such as to generate the alternating layers.

* * * * *